United States Patent
Urch et al.

[11] Patent Number: 5,912,388
[45] Date of Patent: Jun. 15, 1999

[54] PREPARATION OF ALDEHYDES OR KETONES FROM ALCOHOLS

[75] Inventors: Christopher John Urch, Crown Wood, United Kingdom; Istvan Ettienne Marko, Batiment Lavoisier, Belgium; Masao Tuskazaki, Oaza, Japan; Paul Richard Giles, Winneresh; Stephen Martin Brown, Upper Cumberworth, both of United Kingdom

[73] Assignee: Zeneca Limited, United Kingdom

[21] Appl. No.: 08/952,675

[22] PCT Filed: Jul. 4, 1996

[86] PCT No.: PCT/GB96/01607

§ 371 Date: Nov. 12, 1997

§ 102(e) Date: Nov. 12, 1997

[87] PCT Pub. No.: WO97/03033

PCT Pub. Date: Jan. 30, 1997

[30] Foreign Application Priority Data

Jul. 11, 1995 [GB] United Kingdom ............... 9514077
Jun. 12, 1996 [GB] United Kingdom ............... 9612219

[51] Int. Cl.$^6$ .................................................. C07C 45/29
[52] U.S. Cl. ................. 568/320; 568/321; 568/360; 568/402; 568/41; 568/431; 568/471; 546/267; 549/498; 549/70
[58] Field of Search .................... 568/399, 320, 568/321, 360, 402, 41, 431, 471; 546/267; 549/498, 70

[56] References Cited

U.S. PATENT DOCUMENTS

| | | | |
|---|---|---|---|
| 4,380,673 | 4/1983 | Bournonville | 568/361 |
| 4,453,015 | 6/1984 | Slaugh et al. | 568/406 |
| 5,723,679 | 3/1998 | Keshavaraja et al. | 568/406 |

FOREIGN PATENT DOCUMENTS

| | | |
|---|---|---|
| 3705-785 | 1/1988 | Germany . |
| 1154-262 | 7/1985 | U.S.S.R. . |

OTHER PUBLICATIONS

Liu et al, J. Am. Chem. Soc., vol. 115, pp. 3239–3243, 1993.
Jallabert et al, Tetrahedron, vol. 36, pp. 1191–1194. 1980.
Chem. Letters, No. 3, pp. 519–522. 1989.

Liu et al., J. Am. Chem. Soc. 1993, 115, pp. 3239–3243, "The Bis(bipyridine)copper (II)–Induced Activation of Dioxygen for the Catalytic Dehydrogenation of Alcohols".

Yamada et al., The Chemical Society of Japan 1989, pp. 519–522, "Novel Method for Oxidation of Secondary Alcohols into Ketones with Molecular Oxygen by Using Cobalt (II) Complex Catalyst".

Jallabert et al., Tetrahedron vol. 36, pp. 1191–1194, 1980, Great Britain, "Deshydrogenation D'Alcools En Composes Carbonyles Par Le Systeme $CuCl/O_2$/Ligande".

Jallabert et al., Tetrahedron Letters No. 14, pp. 1215–1218, 1977, Great Britain, "Activation de L'Oxygene Moleculaire Par Des Sels De Cuivre Monovalent: Transformation D'Alcools En Aldehydes Par Le Systeme $CuCl$/amine/$O_2$".

Capdevielle et al., Tetrahedron Letters, vol. 25, No. 39, pp. 4397–4400, 1984, Great Britain, "Reaction de L'Oxygene Avec Les Alcoolates de Cuivre I".

Jallabert et al., 78–Inorganic Chem., vol. 94, 1981, p. 693, 57318e, "Molecular oxygen activation by (1, 10–phenanthroline)copper(I) and water activation by (1, 10–phenanthroline)copper(II). Nature and chemical properties of some isolated complexes."

Jallabert et al., 25–Noncondensed Aromatics, vol. 87, 1977, p. 591, 102037f, "Activation of molecular oxygen by monovalent copper salts: rearrangement of alcohols into aldehydes by the cuprous chloride/amine/oxygen system."

Wurm et al., Arch. Pharm. 320, 1987, pp. 564–566, "Reaction of Napthol Derivatives with $CuCl$–$O_2$: A versatile Synthesis of Juglone".

Capdevielle et al., J. Chem. Research (S), 1993, pp. 10–11, "Efficient Catalytic Dehydrogenation of Alcohols by the 2,2'–Bipyridene–Copper(I)Chloride–Dioxygen System in Acetonitrile. A mechanistic Study with Deuterium Isotope Effects".

*Primary Examiner*—James H. Reamer
*Attorney, Agent, or Firm*—David P. LeCroy

[57] ABSTRACT

A process for preparing an aldehyde or ketone comprising reacting a primary or secondary alcohol with oxygen in the presence of a base, a catalytic amount of a copper salt and a suitable lignad under anhydrous conditions.

11 Claims, No Drawings

PREPARATION OF ALDEHYDES OR KETONES FROM ALCOHOLS

The present invention concerns a catalytic oxidative process for preparing aldehydes or ketones from alcohols. Aldehydes and ketones are important intermediates and products in the chemical industry.

The oxidation of certain alcohols to aldehydes or ketones using two equivalents of copper (I) chloride, an amine, oxygen and potassium carbonate is disclosed in Tetrahedron Letters (1977) No.14 1215-8 and Tetrahedron (1980) 36 1191-4.

The present invention provides a process for preparing an aldehyde or ketone comprising reacting a primary or secondary alcohol with oxygen in the presence of a base, a catalytic amount of a copper salt and a suitable ligand under anhydrous conditions.

In one particular aspect the present invention provides a process for preparing an aldellyde or ketone comprising reacting a primary or secondary alcohol with oxygen in the presence of a base, a product obtainable by mixing a catalytic amount of a copper salt and a suitable ligand; the process being conducted under anhydrous conditions.

In another aspect the present invention provides a process for preparing an aldehyde or ketone of formula (I), wherein $R^1$ is hydrogen, optionally substituted alkyl, optionally substituted cycloalkyl, optionally substituted alkenyl, optionally substituted alkynyl, optionally substituted aryl, optionally substituted heteroaryl, optionally substituted aryl$(C_{1-4})$alkyl, optionally substituted heteroaryl$(C_{1-4})$alkyl, optionally substituted aryloxy$(C_{1-4})$alkyl, optionally substituted heteroaryloxy$(C_{1-4})$alkyl; $R^2$ is optionally substituted alkyl, optionally substituted cycloalkyl, optionally substituted alkenyl, optionally substituted alkynyl, optionally substituted aryl, optionally substituted heteroaryl, optionally substituted aryl$(C_{1-4})$alkyl, optionally substituted heteroaryl$(C_{1-4})$alkyl, optionally substituted aryloxy$(C_{1-4})$alkyl, optionally substituted heteroaryloxy$(C_{1-4})$alkyl, optionally substituted arylcarbonyl or optionally substituted heteroarylcarbonyl; or $R^1$ and $R^2$ join to form an optionally substituted carbocyclic ring or an optionally substituted heterocyclic ring; comprising reacting an alcohol of formula (II), wherein $R^1$ and $R^2$ are as defined above, with oxygen in the presence of a base, a catalytic amount of a copper salt and a suitable ligand under anhydrous conditions.

The suitable ligand is a ligand suitable for copper. The ligand is preferably an amine. It is preferably a bidentate ligand such as 1,10-phenanthroline, a substituted 1.10-phenanthroline (for example 5-nitro- 1,10-phenanthroline, 5-chloro-1,10-phenanthroline or 5,6-dioxo-1,10-phenanthroline), a pyridine derivative (such as 2,2'-bipyridine, 4,4'dimethyl-2-2'-bipyridine, 4,4'-bipyridine, 2,2':6',2"-terpyridine or 2,2'-dipyridylamine) or a diamine (such as N,N,N,N-tetrametlhylethiylenediamine or ethyleniediamine).

Oxygen can be supplied in pure form or in the form of air.

It is preferred that the base is a salt such as a carbonate, bicarbonate, alkoxide (provided it is not oxidisable under the reaction conditions, for example tert-butoxide) or acetate of a metal (such as an alkali metal or a transition metal having an atomic number of 21–30). Preferred bases are potassium carbonate, potassium acetate, potassium tert-butoxide, caesium carbonate and sodium carbonate.

A catalytic amount of a copper salt in a sub-stoichiometric amount, preferably 0.9 equivalents or less, more preferably 0.5 equivalents or less. It is preferred that the molar ratio of copper salt:ligand is about 1:1.

In one particular aspect the present invention provides a process wherein the molar ratio of alcohol of formula (II):copper salt:ligand is in the range 1:(0.01–0.10):(0.01–0.10), especially about 1:0.05:0.05.

It is preferred that the copper salt is a copper (I) salt. Preferred counter ions are triflate, acetate, cyanide and, especially, chloride.

The copper salt and ligand interact to form a complex. Thus, in a further aspect the present invention provides a process for preparing an aldehyde or ketone comprising reacting a primary or secondary alcohol with oxygen in the presence of a base and a complex of a copper salt and a suitable ligand; the process being conducted under anhydrous conditions.

In a still further aspect the present invention provides a process for preparing a compound of formula (I), as hereinbefore defined, the process comprising reacting a compound of formula (II), as hereinbefore defined, with oxygen in the presence of a base and a complex of a copper salt and a suitable ligand; the process being conducted under anhydrous conditions.

The process of the present invention is preferably carried out in the presence of a solvent. Suitable solvents include aromatic solvents (such as benzene, toluene, p-xylene, fluorobenzene, perfluorobenzene, iso-butyl benzene or mesitylene), nitrites (such as acetonitrile), hydrocarbon solvents (such as petroleum fractions), halogenated solvents (such as dichloromethane, tetrachloroethylene or 1,2-dichloroethane) or esters (such as methyl or ethyl acetate). Preferred solvents are aromatic solvents (such as toluene, p-xylene, iso-butyl benzene or mesitylene) or hydrocarbon solvents (such as petroleum fractions).

The process of the present invention is carried out under anhydrous conditions, that is, water that is produced as a by-product of the process is either removed from the process environment (such as by azeotropic removal, for example using a Dean and Stark, or similar, apparatus) or the process is conducted in the presence of a drying agent (such as potassium carbonate, magnesium sulphate, sodium sulphate or molecular sieves).

It is preferred that the process of the invention is carried out at elevated temperature, such as in the range 30–140° C., particularly 30–110° C., especially 60–110° C., for example 70–90° C.

The process of the present invention can be carried out at atmospheric pressure, at elevated pressure of up to 10 atmospheres or at autogenic pressure.

Alkyl groups and alkyl moieties have straight or branched chains and, unless stated otherwise, preferably contain from 1 to 24 carbon atoms. Alkyl is, for example, methyl, ethyl, n-propyl, iso-propyl or tert-butyl. Preferred substituents on alkyl groups or moieties include halogen, alkoxy, haloalkoxy, alkylthio, haloalkylthio, cycloalkyl, cyano, nitro, -$NRR^3R^4$, —$NHCOR^3$, —$CONR^3R^4$, —$COOR^3$ or —$COR^3$ in which $R^3$ and $R^4$ are independently hydrogen, $C_{1-4}$ alkyl, $C_{1-4}$ alkoxy, $C_{1-4}$ alkylthio, $C_{3-6}$ cycloalkyl, $C_{3-6}$ cycloalkyl($C_{1-4}$)alkyl, phenyl or benzyl, the phenyl and benzyl groups being optionally substituted with halogen, $C_{1-4}$ alkyl or $C_{1-4}$ alkoxy.

Alkenyl groups have straight or branched chains and, unless stated otherwise, preferably contain from 2 to 24, especially from 2 to 10, carbon atoms. The alkenyl groups contain one or more (preferably 1, 2, 3 or 4) double bonds. Preferred substituents on alkenyl groups include halogen, cycloalkyl, optionally substituted aryl or optionally substituted heteroaryl.

Alkynyl groups have straight or branched chains and, unless stated otherwise, preferably contain from 2 to 24, especially from 2 to 10, carbon atoms. The alkynyl groups contain one or more (preferably 1 or 2) triple bonds. Preferred substituents on alkynyl groups include cycloalkyl, optionally substituted aryl or optionally substituted heteroaryl.

Halogen includes bromine and iodine but is preferably chlorine or fluorine.

Cycloalkyl groups preferably contain from 3 to 7 carbon atoms. Cycloalkyl is, for example, cyclohexyl. Cycloalkyl groups are optionally substituted by halogen or $C_{1-4}$ alkyl.

When $R^1$ and $R^2$ join to form a carbocyclic ring it is preferred that the carbocyclic ring contains 3–9, especially 3–6, carbon atoms and is, for example, a cyclohexane ring. Alternatively, and when $R^1$ and $R^2$ are in a compound of formula (II), $R^1$ and $R^2$ may join to for an aromatic carbocyclic ring which is changed to a non-aromatic ring in the compound of formula (I) as a consequence of the process of the invention. Carbocyclic rings may be fused to one or two optionally substituted aryl or optionally substituted heteroaryl groups.

When $R^1$ and $R^2$ join to form a carbocyclic ring (preferably a cyclohexane, cyclopentane or cyclohexene ring) that ring, may be part of an optionally substituted steroid residue. Thus, compounds of formula (II) include, for example, hydrocholesterol, cholesterol, stigmasterol, ergosterol, diosgenin, anosterol, β-sitosterol, lanosterol, euphol, meldenin, digitoxigenin, inokosterone, ecdysone, artenol and fusisterol; alcohols of gonane, oestrane, androstane, pregnane, cholane and cholestane; and reduced derivatives thereof When $R^1$ and $R^2$ join to form a heterocyclic ring it is preferred that the ring contains 3–9 (for example 5, 6 or 7), especially 3–6, atoms selected from the group comprising carbon, nitrogen, sulphur and oxygen. The heterocyclic ring may be fused to one or two optionally substituted aryl or optionally substituted heteroaryl groups. It is preferred that the heterocyclic ring, comprises 1, 2 or 3 nitrogen, sulphur or oxygen atoms. The heterocyclic ring is, for example, pyrrolidine, piperidine, indoline, morpholine, piperazine, a reduced azepine, oxazole, a reduced pyrimidine, a reduced triazine or a reduced triazole.

The carbocyclic and heterocyclic rings are optionally substituted with one or more of halogen, optionally substituted alkyl, optionally substituted alkenyl, optionally substituted aryl, optionally substituted heteroaryl, optionally substituted aryl($C_{1-4}$)alkyl, optionally substituted heteroaryl ($C_{1-4}$)alkyl, optionally substituted aryloxy($C_{1-4}$)alkyl, optionally substituted heteroaryloxy($C_{1-4}$)alkyl or optionally substituted non-aromatic heterocycle.

Aryl includes naphtlhyl and phenyl.

Aryl, heteroaryl, phenyl or non-aromatic heterocycle groups can be optionally substituted with one or more of the following: halogen, $C_{1-4}$ alkyl (especially methyl and ethyl), $C_{2-4}$ alkenyl (especially allyl), $C_{2-4}$ alkynyl (especially propargyl), $C_{1-4}$ alkoxy (especially methoxy), $C_{2-4}$ alkenyloxy (especially allyloxy), $C_{2-4}$ alkynyloxy (especially propargyloxy), halo($C_{1-4}$)alkyl (especially trifluoromethyl), halo($C_{1-4}$)alkoxy (especially trifluoromethoxy), $C_{1-4}$ alkylthio (especially methylthio), halo($C_{1-4}$)alkylthio, $C_{1-4}$alkoxy($C_{1-4}$)alkyl, $C_{3-6}$ cycloalkyl, $C_{3-6}$ cycloalkyl($C_{1-4}$)alkyl, optionally substituted methylenedioxy (especially optionally substituted with fluorine or $C_{1-4}$ alkyl), optionally substituted aryl (especially optionally substituted phenyl), optionally substituted aryloxy (especially optionally substituted phenoxy), optionally substituted aryl ($C_{1-4}$)alkyl (especially optionally substituted benzyl, optionally substituted phenethyl and optionally substituted phenyl n-propyl), optionally substituted aryl($C_{2-4}$)alkenyl (especially optionally substituted phenylethenyl), optionally substituted aryl($C_{1-4}$)alkoxy (especially optionally substituted benzyloxy), optionally substituted aryloxy($C_{1-4}$)alkyl (especially phenoxymethyl), acyloxy (including $C_{1-4}$ alkanoyloxy (especially acetyloxy) and benzoyloxy), cyano, thiocyanato, nitro, —NR'R", —NHCOR', —NHCONR'R", —CONR'R", —COOR', —OSO$_2$R', —SO$_2$R', —COR', —CR'=NR" or —N=CR'R" in which R' and R" are independently hydrogen, $C_{1-4}$ alkyl, $C_{1-4}$ alkoxy, $C_{1-4}$ alkylthio, $C_{3-6}$ cycloalkyl, $C_{3-6}$ cycloalkyl($C_{1-4}$)alkyl, phenyl or benzyl, the phenyl and benzyl groups being optionally substituted with halogen, $C_{1-4}$ alkyl or $C_{1-4}$ alkoxy; or two substituents, when they are in adjacent positions on the aryl ring can join to form a fused aliphatic ring (especially to form a fused 6-membered carbon aliphatic ring).

Substituents which may be present in the aryl ring of any of the foregoing substituents include one or more of the following: halogen, $C_{1-4}$ alkyl, $C_{2-4}$ alkenyl, $C_{2-4}$alkynyl, $C_{1-4}$ alkoxy, $C_{2-4}$ alkenyloxy, $C_{2-4}$- alkynyloxy, halo($C_{1-4}$) alkyl, halo ($C_{1-4}$)alkoxy, $C_{1-4}$ alkylthio, $C_{1-4}$ alkoxy($C_{1-4}$) alkyl, $C_{3-6}$ cycloalkyl, $C_{3-6}$ cycloalkyl($C_{1-4}$)alkyl, alkanoyloxy, benzoyloxy, cyano, thiocyanato, nitro, —NR'R", —NHCOR', —NHCONR'R", —CONR'R", —COOR', —SO$_2$R', —OSO$_2$R', —COR', —CR'=NR" or —N=CR'R" in which R' and R" have the meanings given above.

Heteroaryl rings are preferably 5 or 6-membered ring systems comprising 1, 2 or 3 oxygen, sulphur or nitrogen atoms. Heteroaryl is, for example, furan, thiophen, pyridine, pyrimidine, pyrrole, pyrazole, quinoline, isoquinoline, 1,2, 4-triazole, imidazole, a triazine (1,2,3-, 1,2,4- or 1,3,5-), oxadiazole, thiadiazole, oxazole, thiazole or isoxazole.

Non-aromatic heterocycle includes azetidine, pyrrolidine, piperidine or morpholine.

In yet another aspect the present invention provides a process for preparing an aldehyde or ketone of formula (I), wherein R' is hydrogen, optionally substituted alkyl, optionally substituted cycloalkyl, optionally substituted alkenyl, optionally substituted alkynyl, optionally substituted aryl, optionally substituted heteroaryl, optionally substituted aryl ($C_{1-4}$)alkyl, optionally substituted heteroaryl($C_{1-4}$)alkyl, optionally substituted aryloxy($C_{1-4}$)alkyl, optionally substituted heteroaryloxy($C_{1-4}$)alkyl; $R^2$ is optionally substituted alkyl, optionally substituted cycloalkyl, optionally substituted alkenyl, optionally substituted alkynyl, optionally substituted aryl, optionally substituted heteroaryl, optionally substituted aryl($C_{1-4}$)alkyl, optionally substituted heteroaryl ($C_{1-4}$)alkyl, optionally substituted aryloxy($C_{1-4}$)alkyl, optionally substituted heteroaryloxy($C_{1-4}$)alkyl, optionally substituted arylcarbonyl or optionally substituted heteroarylcarbonyl; or $R^1$ and $R^2$ join to form an optionally substituted carbocyclic ring or an optionally substituted heterocyclic ring; comprising reacting an alcohol of formula (II), wherein $R^1$ and $R^2$ are as defined above, with oxygen in the presence of a base, a product obtainable by mixing a catalytic amount of a copper salt and a suitable ligand; the process being conducted under anhydrous conditions.

In a further aspect the present invention provides a process as described above wherein $R^1$ is hydrogen, alkyl or optionally substituted aryl; and $R^2$ is alkyl, alkenyl optionally substituted by phenyl, optionally substituted aryl, optionally substituted heteroaryl or optionally substituted arylcarbonyl; or $R^1$ and $R^2$ join to form a carbocyclic ring optionally substituted with alkyl or alkenyl.

In a still further aspect the present invention provides a process for preparing an aldehyde or ketone of formula (I), wherein $R^1$ is hydrogen, optionally substituted alkyl, optionally substituted cycloalkyl, optionally substituted alkenyl, optionally substituted alkynyl, optionally substituted aryl, optionally substituted heteroaryl, optionally substituted aryl$(C_{1-4})$alkyl, optionally substituted heteroaryl$(C_{1-4})$alkyl, optionally substituted aryloxy$(C_{1-4})$alkyl, optionally substituted heteroaryloxy$(C_{1-4})$alkyl; $R^2$ is optionally substituted alkyl, optionally substituted cycloalkyl, optionally substituted alkenyl, optionally substituted alkynyl, optionally substituted aryl, optionally substituted heteroaryl, optionally substituted aryl$(C_{1-4})$alkyl, optionally substituted heteroaryl$(C_{1-4})$alkyl, optionally substituted aryloxy$(C_{1-4})$alkyl, optionally substituted heteroaryloxy$(C_{1-4})$alkyl, optionally substituted arylcarbonyl or optionally substituted heteroarylcarbonyl; or $R^1$ and $R^2$ join to form an optionally substituted carbocyclic ring or an optionally substituted heterocyclic ring; the process comprising reacting an alcohol of formula (II), wherein $R^1$ and $R^2$ are as defined above, with oxygen in the presence of a base, a catalytic amount of a copper salt, a suitable ligand and a reducing agent under anhydrous conditions.

In another aspect the present invention provides a process for preparing a compound of formula (I) wherein $R^1$ is hydrogen, alkyl or optionally substituted aryl; and $R^2$ is alkyl, alkenyl optionally substituted by phenyl, optionally substituted aryl, optionally substituted heteroaryl or optionally substituted arylcarbonyl; or $R^1$ and $R^2$ join to form a carbocyclic ring optionally substituted with alkyl or alkenyl; the process comprising reacting an alcohol of formula (II), with oxygen in the presence of a base, a catalytic amount of a copper salt, a suitable ligand and a reducing agent under anhydrous conditions.

In yet another aspect the present invention provides a process for preparing an aldehyde or ketone of formula (I), wherein $R^1$ is hydrogen, optionally substituted alkyl, optionally substituted cycloalkyl, optionally substituted alkenyl, optionally substituted alkynyl, optionally substituted aryl, optionally substituted heteroaryl, optionally substituted aryl$(C_{1-4})$alkyl, optionally substituted heteroaryl$(C_{1-4})$alkyl, optionally substituted aryloxy$(C_{1-4})$alkyl, optionally substituted heteroaryloxy$(C_{1-4})$alkyl; $R^2$ is optionally substituted alkyl, optionally substituted cycloalkyl, optionally substituted alkenyl, optionally substituted alkynyl, optionally substituted aryl, optionally substituted heteroaryl, optionally substituted aryl$(C_{1-4})$alkyl, optionally substituted heteroaryl$(C_{1-4})$alkyl, optionally substituted aryloxy$(C_{1-4})$alkyl, optionally substituted heteroaryloxy$(C_{1-4})$alkyl, optionally substituted arylcarbonyl or optionally substituted heteroarylcarbonyl; or $R^1$ and $R^2$ join to form an optionally substituted carbocyclic ring, or an optionally substituted heterocyclic ring; the process comprising reacting an alcohol of formula (II), wherein $R^1$ and $R^2$ are as defined above, with oxygen in the presence of a base, a reducing agent, a product obtainable by mixing a catalytic amount of a copper salt and a suitable ligand; the process being conducted under anhydrous conditions.

Suitable reducing agents include hydrazine or a derivative thereof (such as a 1,2 dicarb$(C_{1-4})$alkoxyhydrazine (for example 1,2-dicarbethoxyhydrazine, 1,2-dicarbmethoxyhydrazine or 1,2-dicarb-tert-butoxyhydrazine), (2,4-dinitrophenyl)hydrazine, tosylhydrazine or an alkylhydrazine (for example dimethylhydrazine)), or a compound which produces a hydrazine under the reaction conditions (such as a di($C_{1-4}$alkyl)diazodicarboxylate, for example diethyl diazodicarboxylate, dimethyl diazodicarboxylate or di-tert-butyl diazodicarboxylate). It is preferred that the molar ratio of reducing agent:copper salt is 1:(0.5–4.0), especially 1:(0.9–2.5), for example about 1:1 or about 1:2.

In another aspect the present invention provides a process for preparing a compound of formula (I) as hereinbefore defined, the process comprising, reacting an alcohol of formula (II), with oxygen in the presence of a drying agent (such as potassium carbonate or molecular sieves), a base (such as potassium carbonate or potassium tert-butoxide), a catalytic amount of a copper (I) salt (such as copper (I) chloride), a suitable ligand (such as 1,10-phenanthroline) and a reducing agent (such as 1,2-dicarbethoxyhydrazine).

In a further aspect the present invention provides a process as hereinbefore described for preparing a compound of formula (I) wherein $R^1$ is hydrogen, $C_{1-24}$ alkyl or phenyl; $R^2$ is $C_{1-24}$ alkyl, $C_{2-24}$ alkenyl, $C_{2-24}$ alkenyl substituted with a phenyl group, pyridyl, furyl, thienyl or benzoyl; or $R^1$ and $R^2$ join to form a carbocyclic ring optionally substituted with alkyl; phenyl groups of the foregoing being optionally substituted by halogen, $C_{1-4}$ alkyl, $C_{1-4}$ alkoxy, $C_{1-4}$ haloalkoxy, $C_{2-4}$ alkenyl, $C_{2-4}$ alkynyl, $C_{1-4}$ haloalkyl, $C_{1-4}$ alkoxy$(C_{1-4})$alkyl, cyano or nitro.

The process of the present invention is preferably conducted by mixing a catalytic amount of a copper salt and suitable ligand in an organic solvent and then adding a drying agent, base, alcohol and, where appropriate, a reducing agent. Oxygen or air is then bubbled into the reaction mixture and the reaction mixture is heated. Once the process has gone to completion the product can be separated by either:

neutralising the reaction mixture with an acid (preferably a strong mineral acid such as hydrochloric acid), and separating the organic phase which contains the product; or, filtrating the reaction mixture and washing the residue to leave the filtrate which contains the product.

The following Examples illustrate the process of the invention.

EXAMPLE 1

This Example illustrates the preparation of p-chlorobenzaldehyde.

To a stirred mixture of toluene (12 ml) and copper (I) chloride (12.5 mg) were added 1,10-phenanthroline (24 mg), powdered 4 Å sieves (1 g, ex-Fluka, flame-dried), potassium tert-butoxide (0.28 g), 1,2-dicarbethoxyhydrazine (0.11 g) and p-chlorobenzyl alcohol (0.36 g). Oxygen was bubbled into the reaction mixture and the reaction mixture was stirred at 80° C. Ater 45 minutes at 80° C. analysis showed 100% conversion of p-chlorobenzyl alcohol to p-chlorobenzaldehyde.

EXAMPLE 2

This Example illustrates the preparation of p-chlorobenzaldehyde.

To a stirred mixture of toluene (600 ml) and copper (I) chloride (1.24 g) was added 1,10-phenanthroline (2.26 g). A complex was allowed to form, as a black-grey solid, before potassium carbonate (70 g) was added, followed by 1,2-dicarbethoxyhydrazine (11 ) and then p-chlorobenzyl alcohol (35.6 g). This was heated to 80–90° C. and gentle current of air was added via a sintered inlet. Aliquots of the solution were taken at intervals and analysed by $^1$H NMR spectroscopy. The reaction was judged to be complete at 5 h, and was allowed to cool. The crude reaction mixture was transferred to a 1l separating funnel and dilute hydrochloric acid was added slowly until the aqueous phase was acidic. The aqueous layer was extracted with toluene (2×100 ml); the combined organic layers washed with saturated aqueous sodium bicarbonate (100 ml) and brine (100 ml) and dried (MgSO$_4$). The solvent was evaporated to leave 34.1 g of a sticky black oil; purity of product ($^1$H NMR~85%). The residue was re-crystallised from ethanol-water (3:1) to give p-chlorobenzaldehyde.

EXAMPLE 3

This Example illustrates the preparation of citral.

Following the procedure of Example 2 but using geraniol in place of p-chlorobenzyl alcohol and 5 mol % of copper (I) chloride and 1,10-phenanthroline gave the title compound in 80% conversion (by $^1$H NMR analysis) after 6 hours.

EXAMPLE 4

This Example illustrates the preparation of acetophenone.

Following the procedure of Example 2 but using 1-phenylethanol in place of p-chlorobenzyl alcohol and 5 mol % copper (I) chloride and 1,10-phenanthroline gave the title compound in 100% conversion (by $^1$NMR analysis) after 1 hour.

Using similar methodology $C_6H_5CH(OH)CF_3$ was converted to $C_6H_5C(O)CF_3$.

EXAMPLE 5

This Example illustrates the preparation of cinnamyl aldehyde.

Following the procedure of Example 2 but using cinnamyl alcohol in place of p-chlorobenzyl alcohol and 5 mol % copper (I) chloride and 1,10-phenantliroline gave the title compound in 100% conversion (by $^1$H NMR analysis) after 1 hour.

EXAMPLE 6

This Example illustrates the preparation of benzil.

Following the procedure of Example 2 but using benzoin in place of p-chlorobenzyl alcohol and 5 mol % copper (I) chloride and 1,10-phenantholine gave the title compound in 100% conversion (by $^1$H NMR analysis) after 3 hours.

EXAMPLE 7

This Example illustrates the preparation of 4-tert-butyl-cyclohexanone.

Following the procedure of Example 2 but using trans-4-tert-butylcyclohexanol in place of p-chlorobenzyl alcohol and 20 mol % copper (I) chloride and 1,10-phenanthroline gave the title compound in 60% conversion (by $^1$H NMR analysis) after 4 hours.

EXAMPLE 8

This Example illustrates the preparation of 4-tert-butylcyclohexanone.

Following the procedure of Example 7 but using cis-4-tert-butylcyclohexanol in place of trans-4-tert-butylcyclohexanol gave the title compound in 70% conversion (by $^1$H NMR analysis) after 4 hours.

EXAMPLE 9

This Example illustrates the preparation of 5-undecanone.

Following the procedure of Example 7 but using 5-undecanol in place of trans-4-tert-butyl-cyclohexanol gave the title compound in 90% conversion (by $^1$H NMR analysis) after 16 hours.

EXAMPLE 10

This Example illustrates the preparation of 2-undecanone.

Following the procedure of Example 2 but using 2-undecanol in place of p-chlorobenzyl alcohol and 33 mol % copper (I) chloride and 1,10-phenanthroline gave the title compound in 44% conversion (by $^1$NMR analysis) after 6 hours.

EXAMPLE 11

This Example illustrates the preparation of p-chlorobenzaldehyde.

A solution of anhydrous hydrazine was prepared from a commercial solution of hydrazine by azeotropic distillation with toluene, to give an approximately 1M solution. Following the procedure of Example 2 using hydrazine in toluene (12 ml, 1M), copper (I) chloride (12.5 mg), 1,10-phenanthroline (24 mg), potassium carbonate (0.7 g), and p-chlorobenzyl alcohol (0.36 g). The reaction was stirred at 80° C. and after 2 hours $^1$H NMR analysis showed 100% conversion to the title compound.

EXAMPLE 12

This Example illustrates the preparation of 2-pyridinecarboxaldehyde.

Copper (I) chloride (12.5 mg) and 1,10-phenanthroline (24 mg) were added to toluene (12 ml) with stirring. Potassium carbonate (0.7 g), 1,2-dicarbethoxyhydrazine (0.11 g) and pyridine-2-methanol (0.27 g) were then added to the reaction mixture. Oxygen was bubbled into the mixture and the mixture was stirred at 80° C. for 4 hours. $^1$H NMR analysis of the reaction mixture showed a 94% conversion to the title compound.

EXAMPLE 13

This Example illustrates the preparation of 2-thiophenecarboxaldehyde.

Following the procedure of Example 12 but using thiophen-2-methanol in place of pyridine-2-methanol gave the title compound in 100% conversion ($^1$H NMR analysis) after 1 hour.

EXAMPLE 14

This Example illustrates the preparation of 2-furancarboxaldehyde.

Following the procedure of Example 12 but using furfuryl alcohol in place of pyridine-2-methanol gave the title compound in 100% conversion ($^1$H NMR analysis) after 2 hours.

EXAMPLE 15

This Example illustrates the preparation of p-chlorobenzaldehyde.

Copper (I) chloride (12.5 mg) and 1,10-phenanthroline (24 mg) were suspended in toluene (12 ml) in a flask equipped with a Dean and Stark apparatus. 1,2-Dicarbethoxyhydrazine (0.11 g), potassium tert-butoxide (28 mg) and p-chlorobenzylalcohol (0.36 g) were then added to the reaction mixture. Oxygen was bubbled into the mixture and the mixture was stirred at reflux. $^1$H NMR analysis of the reaction mixture showed 100% conversion to the title compound after 3 hours.

EXAMPLE 16

This Example illustrates the preparation of p-chlorobenzaldehyde.

Copper (I) chloride (12.5 mg) and 1,10-phenantliroline (24 mg) were suspended in toluene (12 ml). Potassium carbonate (0.7 g), diethyl diazodicarboxylate (0.11 g) and p-chlorobenzylalcohol (0.36 g) were added sequentially to the reaction mixture. Oxygen was bubbled into the mixture and the mixture was stirred at reflux. $^1$H NMR analysis of the reaction mixture showed 100% conversion to the title compound after 0.5 hours.

EXAMPLE 17

This Example illustrates the preparation of p-chlorobenzaldehyde.

Copper (I) chloride (10 mg) and 1,10-phenanthroline (18 mg) were suspended in toluene (5 ml). 4 Å molecular sieves, di-tert-butyl diazodicarboxylate (0.276 g) and p-chlorobenzylalcohol (0.143 g) were added successively and the resulting mixture was stirred for 12 hours at room temperature whilst oxygen was bubbled in. After dilution with diethyl ether (10 ml), the reaction mixture was filtered and the filtrate evaporated in vacuo to leave the title compound in 99% yield and 100% conversion.

EXAMPLE 18

This Example illustrates the preparation of p-chlorobenzaldehyde.

To a mixture of copper (I) chloride (1.98 g) and 1,10-phenanthroline (3.60 g) were added toluene (800 ml) and potassium carbonate (110 g). The resulting mixture was stirred for 30 minutes after which di-tert-butyl azodicarboxylate (4.60 g) and p-chlorobenzylalcohol (57.0 g) were added successively. The mixture was heated to 90° C. and oxygen gas was bubbled in for 1.5 hours. After cooling to room temperature the reaction mixture was diluted with diethyl ether (500 ml) and filtered through a pad of CELITE™. The filtrate was washed successively with water (200 ml), 1N aqueous hydrochloric acid (200 ml) and brine (200 ml), dried over magnesium sulphate and evaporated in vacuo. The resulting residue was distilled to provide the title compound (46.5 g, 83% yield).

EXAMPLES 19–39

The following procedure was followed for Examples 19–39.

Toluene (10 ml) was added to a mixture of copper (I) chloride (0.10 mmol, 5 mol % to alcohol) and 1,10-phenanthroline (0.10 mmol, 5 mol % to alcohol). The mixture was stirred at of room temperature for 10 minutes and a black-grey precipitate formed. To this were added successively potassium carbonate (4.00 mmol, 200 mol % to alcohol), a reducing agent [1,2-dicarb-tert-butoxyhydrazine (DBAD-H$_2$) or di-tert-butyl diazodicarboxylate (DBAD)] (0.10 mmol, 5 mol % to alcohol) and a primary or secondary alcohol (2.00 mmol). The resulting mixture was heated to 90° C. and oxygen was bubbled in for a period of time (T). The reaction mixture was then cooled to room temperature, diluted with diethyl ether (10 ml) and filtered through a pad of CELITE™. The filtrate was filtered in vacuo and the residue purified by silica gel column chromatography (eluting with ethyl acetate:hexane 1:10–1:5) to provide aldehyde or ketone.

Results for Examples 19–39 are provided in the Table below.

| Example No | Alcohol | Reducing Agent | T | Conversion (%) | Yield (%)[a] |
|---|---|---|---|---|---|
| 19 | p-Chlorobenzyl alcohol | DBAD-H$_2$ | 0.75 | 100 | 90 |
| 20[b] | p-Chlorobenzyl alcohol | DBAD | 1 | 100 | 83[e] |
| 21 | Cinnamyl alcohol | DBAD-H$_2$ | 1 | 100 | 89 |
| 22 | Cinnamyl alcohol | DBAD | 1 | 100 | 80 |
| 23 | Geraniol | DBAD-H$_2$ | 1 | 75 | 67 |
| 24[d] | Geraniol | DBAD-H$_2$ | 1 | 86 | 74 |
| 25 | Geraniol | DBAD | 1 | 74 | 71 |
| 26 | Nerol | DBAD-H$_2$ | 1 | 83 | 73 |
| 27 | 1-Decanol | DBAD-H$_2$ | 0.75 | 80[e] | 63[e] |
| 28[d] | 1-Decanol | DBAD-H$_2$ | 0.75 | 87[e] | 72[e] |
| 29 | 1-Decanol | DBAD | 0.75 | 74[e] | 58[e] |
| 30 | 2-Undecanol | DBAD-H$_2$ | 2 | 86 | 86 |
| 31 | 2-Undecanol | DBAD | 2 | 90 | 88 |
| 32 | 4-tert-Butylcyclohexanol | DBAD-H$_2$ | 2 | 59 | 57 |
| 33[f] | 4-tert-Butylcyclohexanol | DBAD-H$_2$ | 2 | 71 | 68 |
| 34[d] | 4-tert-Butylcyclohexanol | DBAD-H$_2$ | 2 | 80 | 76 |
| 35[g] | 4-tert-Butylcyclohexanol | DBAD | 2 | 87 | 84 |
| 36[g] | Hydrocholesterol | DBAD | 2 | 74 | 70 |
| 37 | p-(Methylthio)benzyl alcohol | DBAD-H$_2$ | 1 | 95 | 92 |
| 38 | 3-Pyridylcarbinol | DBAD-H$_2$ | 1 | 92 | 81 |
| 39 | α-Trifluoromethyl-2-naphthalenemethanol | DBAD | 1 | 99 | 92 | a = isolated yield unless otherwise noted
b = reaction carried out on 0.4 mol scale
c = determined after distillation
d = copper (I) chloride, 1,10-phenanthroline and DBAD-H$_2$ used at 10 mol % to alcohol
e = determined by gas chromatography using tetradecane as internal standard
f = DBAD-H$_2$ used at 10 mol % to alcohol
g = copper (I) chloride, 1,10-phenanthroline and DBAD used at 10 mol % to alcohol CHEMICAL FORMULAE
(In Description)

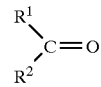

(I)

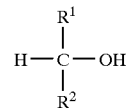

(II)

We claim:
1. A process for preparing an aldehyde or ketone of formula (I):

(I)

wherein R$^1$ is hydrogen, alkyl, cycloalkyl, alkenyl, alkynyl, aryl, heteroaryl, aryl(C$_{1-4}$)alkyl, heteroaryl(C$_{1-4}$)alkyl, aryloxy(C$_{1-4}$)alkyl, heteroaryloxy(C$_{1-4}$)alkyl; R$^2$ is alkyl cycloalkyl, alkenyl, alkynyl, aryl, heteroaryl, aryl(C$_{1-4}$) alkyl, heteroaryl(C$_{1-4}$)alkyl, aryloxy(C$_{1-4}$)alkyl, heteroaryloxy(C$_{1-4}$)alkyl, arylcarbonyl or heteroarylcarbonyl; or R$^1$ and R$^2$ join to form a carbocyclic ring or a heterocyclic ring; carbocyclic and heterocyclic rings are optionally substituted with one or more of halogen, optionally substituted alkyl, optionally substituted alkenyl, optionally substituted aryl, optionally substituted heteroaryl, optionally substituted aryl($C_{1-4}$)alkyl, optionally substituted heteroaryl($C_{1-4}$)alkyl, optionally substituted aryloxy($C_{1-4}$)alkyl, optionally substituted heteroaryloxy($C_{1-4}$)alkyl or optionally substituted non-aromatic heterocycle; alkyl groups or moieties are optionally substituted by halogen, alkoxy, haloalkoxy, alkylthio, haloalkylthio, cycloalkyl, cyano, nitro, —$NR^3R^4$, —$NHCOR^3$, —$CONR^3R^4$, —$COOR^3$ or —$COR^3$ in which $R^3$ and $R^4$ are independently hydrogen, $C_{1-4}$ alkyl, $C_{1-4}$ alkoxy, $C_{1-4}$ alkylthio, $C_{3-6}$ cycloalkyl, $C_{3-6}$ cycloalkyl($C_{1-4}$)alkyl, phenyl or benzyl, the phenyl and benzyl groups being optionally substituted with halogen, $C_{1-4}$alkyl or $C_{1-4}$ alkoxy; alkenyl groups are optionally substituted by halogen, cycloalkyl, optionally substituted aryl or optionally substituted heteroaryl; alkynyl groups are optionally substituted by cycloalkyl, optionally substituted aryl or optionally substituted heteroaryl; cycloalkyl groups are optionally substituted by halogen or $C_{1-6}$ alkyl; aryl, heteroaryl, phenyl or non-aromatic heterocycle groups are optionally substituted with one or more of the following: halogen, $C_{1-4}$ alkyl, $C_{2-4}$ alkenyl, $C_{2-4}$ alkynyl, $C_{1-4}$alkoxy, $C_{2-4}$ alkenyloxy, $C_{2-4}$ alkynyloxy, halo($C_{1-4}$)alkyl, halo($C_{1-4}$)alkoxy, $C_{1-4}$alkylthio, halo($C_{1-4}$)alkylthio, $C_{1-4}$alkoxy($C_{1-4}$)alkyl, $C_{3-6}$ cycloalkyl, $C_{3-6}$cycloalkyl($C_{1-4}$)alkyl, methylenedioxy (optionally substituted with fluorine or $C_{1-4}$alkyl), optionally substituted aryl, optionally substituted aryloxy, optionally substituted aryl($C_{1-4}$)alkyl, optionally substituted aryl($C_{2-4}$)alkenyl, optionally substituted aryl($C_{1-4}$)alkoxy, optionally substituted aryloxy($C_{1-4}$)alkyl, acyloxy, cyano, thiocyanato, nitro, —NR'R", —NHCOR', —NHCONR'R", —CONR'R", —COOR', —$OSO_2R'$, —$SO_2R'$, —COR', —CR'=NR" or —N=CR'R"; or two substituents, when they are in adjacent positions on the aryl ring can join to form a fused aliphatic ring; substituents which may be present in the aryl ring of any of the foregoing substituents include one or more of the following: halogen, $C_{1-4}$alkyl, $C_{2-4}$alkenyl, $C_{2-4}$alkynyl, $C,_{1-4}$ alkoxy, $C_{2-4}$alkenyloxy, $C_{2-4}$alkynyloxy, halo($C_{1-4}$)alkyl, halo($C_{1-4}$)alkoxy, $C_{1-4}$alkylthio, $C_{1-4}$ alkoxy($C_{1-4}$)alkyl, $C_{3-6}$cycloalkyl, $C_{3-6}$cycloalkyl($C_{1-4}$)alkyl, alkanoyloxy, benzoyloxy, cyano, thiocyanato, nitro, —NR'R", —NHCOR, —NHCONR'R", —CONR'R", —COOR', —$SO_2R'$, —$OSO_2R'$, —COR', —CR'=NR" or —N=CR'R"; R' and R" are independently hydrogen, $C_{1-4}$alkyl, $C_{1-4}$alkoxy, $C_{1-4}$alkylthio, $C_{3-6}$cycloalkyl, $C_{3-6}$cycloalkyl($C_{1-4}$)alkyl, phenyl or benzyl, the phenyl and benzyl groups being optionally substituted with halogen, $C_{1-4}$alkyl or $C_{1-4}$alkoxy; the process comprising reacting an alcohol of formula (II):

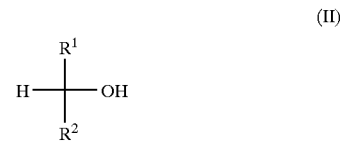

wherein $R^1$ and $R^2$ are as defined above, with oxygen in the presence of:
  i. as a base: a carbonate, bicarbonate, alkoxide (provided it is not oxidisable under the reaction conditions) or acetate of an alkali metal or a transition metal having an atomic number of 21–30;
  ii. a catalytic amount of a copper (I) salt; and,
  iii. as a bidentate ligand: 1,10-phenanthroline, a substituted 1,10-phenanthroline, a pyridine derivative or a diamine;
under anhydrous conditions.

2. A process as claimed in claim 1 wherein the process is carried out in the presence of a reducing agent.

3. A process as claimed in claim 2 wherein the copper salt is copper (I) chloride.

4. A process as claimed in claim 2 wherein the molar ratio of alcohol of formula (II):copper (I) salt:ligand is in the range 1:(0.01–0.10):(0.01–0.10).

5. A process as claimed in claim 2 wherein the molar ratio of copper (I) salt:ligand is about 1:1.

6. A process as claimed in claim 2 wherein the process is carried out in a solvent.

7. A process as claimed in claim 1 wherein the process is carried out in a solvent.

8. A process as claimed in claim 1 wherein the copper salt is copper (I) chloride.

9. A process as claimed in claim 2 wherein the reducing agent is a hydrazine or derivative thereof, or a compound that produces a hydrazine under the reaction conditions.

10. A process as claimed in claim 1 wherein the molar ratio of alcohol of formula (II):copper (I) salt:ligand is in the range 1:(0.01–0.10):(0.01–0.10).

11. A process as claimed in claim 1 wherein the molar ratio of copper (I) salt:ligand is about 1:1.

* * * * *